(12) United States Patent
Rezai et al.

(10) Patent No.: US 8,989,862 B2
(45) Date of Patent: Mar. 24, 2015

(54) APPARATUS AND METHOD FOR TREATING PULMONARY CONDITIONS

(75) Inventors: Ali R. Rezai, Shaker Heights, OH (US); Milind Deogaonkar, Broadview Heights, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 7 days.

(21) Appl. No.: 13/210,613

(22) Filed: Aug. 16, 2011

(65) Prior Publication Data
US 2011/0301679 A1  Dec. 8, 2011

Related U.S. Application Data

(60) Division of application No. 12/129,734, filed on May 30, 2008, which is a continuation-in-part of application No. 12/016,115, filed on Jan. 17, 2008.

(60) Provisional application No. 60/932,248, filed on May 30, 2007.

(51) Int. Cl.
*A61N 1/36* (2006.01)
*A61N 1/05* (2006.01)

(52) U.S. Cl.
CPC ............ *A61N 1/0553* (2013.01); *A61N 1/3611* (2013.01); *A61N 1/0519* (2013.01); *A61N 1/0556* (2013.01); *A61N 1/36114* (2013.01)
USPC .......................................................... 607/42

(58) Field of Classification Search
CPC ........................... A61N 1/3611; A61N 1/0519
USPC .......................................................... 607/42
See application file for complete search history.

(56) References Cited

U.S. PATENT DOCUMENTS

| 4,795,465 A | 1/1989 | Marten |
| 5,024,228 A | 6/1991 | Goldstone et al. |

(Continued)

FOREIGN PATENT DOCUMENTS

| RU | 2 108 817 C1 | 4/1998 |
| WO | WO-93/01862 A1 | 2/1993 |

OTHER PUBLICATIONS

Gromova et al., "Sinusoidal Modulated Currents in Comprehensive Treatment of Children with Bronchial Asthma", *Voprosy kurortologii fizioterapii, i lechebnoi fizicheskoi kultury*, May-Jun; (3):45-7 (1981).

(Continued)

*Primary Examiner* — Eric D. Bertram
(74) *Attorney, Agent, or Firm* — Tarolli, Sundheim, Covell & Tummino LLP

(57) ABSTRACT

A method for treating a pulmonary condition in a subject is provided. One step of the method includes providing an apparatus for positioning at a target site innervated by at least one nerve of the autonomic nervous system (ANS). The apparatus includes a fluid exchange catheter, an inflatable balloon coupled to the fluid exchange catheter, and an energy delivery mechanism including at least one energy delivery member for delivering electrical energy to the target site. Next, an expansion medium is delivered to the apparatus so that the inflatable balloon is sufficiently inflated to sandwich at least a portion of the at least one energy delivery member between the inflatable balloon and a luminal wall of the tracheo-bronchial tree at the target site. Electrical energy is then delivered to the at least one energy delivery member to effect a change in the ANS of the subject.

18 Claims, 7 Drawing Sheets

(56) References Cited

U.S. PATENT DOCUMENTS

| | | | |
|---|---|---|---|
| 5,125,406 A | 6/1992 | Goldstone et al. | |
| 5,379,765 A | 1/1995 | Kajiwara et al. | |
| 5,584,290 A | 12/1996 | Brain | |
| 5,716,377 A | 2/1998 | Rise et al. | |
| 6,058,331 A | 5/2000 | King | |
| 6,104,957 A | 8/2000 | Alo et al. | |
| 6,198,970 B1 | 3/2001 | Freed et al. | |
| 6,266,548 B1 | 7/2001 | Lamade et al. | |
| 6,266,564 B1 | 7/2001 | Hill et al. | |
| 6,292,695 B1 | 9/2001 | Webster, Jr. et al. | |
| 6,411,852 B1 | 6/2002 | Danek et al. | |
| 6,425,877 B1 | 7/2002 | Edwards | |
| 6,449,507 B1 | 9/2002 | Hill et al. | |
| 6,532,388 B1* | 3/2003 | Hill et al. | 607/2 |
| 6,572,543 B1 | 6/2003 | Christopherson et al. | |
| 6,633,779 B1 | 10/2003 | Schuler et al. | |
| 6,748,275 B2 | 6/2004 | Lattner et al. | |
| 6,885,888 B2 | 4/2005 | Rezai | |
| 7,027,869 B2 | 4/2006 | Danek et al. | |
| 7,072,720 B2 | 7/2006 | Puskas | |
| 7,200,445 B1 | 4/2007 | Dalbec et al. | |
| 7,277,757 B2 | 10/2007 | Casavant et al. | |
| 7,340,299 B2 | 3/2008 | Puskas | |
| 2002/0010495 A1 | 1/2002 | Freed et al. | |
| 2002/0032468 A1 | 3/2002 | Hill et al. | |
| 2002/0107553 A1 | 8/2002 | Hill et al. | |
| 2002/0165586 A1 | 11/2002 | Hill et al. | |
| 2003/0004549 A1 | 1/2003 | Hill et al. | |
| 2003/0045909 A1 | 3/2003 | Gross et al. | |
| 2003/0074039 A1* | 4/2003 | Puskas | 607/118 |
| 2003/0093128 A1 | 5/2003 | Freed et al. | |
| 2003/0100924 A1 | 5/2003 | Foreman et al. | |
| 2003/0181951 A1 | 9/2003 | Cates | |
| 2003/0181958 A1 | 9/2003 | Dobak, III | |
| 2003/0181959 A1 | 9/2003 | Dobak, III | |
| 2004/0030362 A1 | 2/2004 | Hill et al. | |
| 2004/0153127 A1 | 8/2004 | Gordon et al. | |
| 2004/0230251 A1 | 11/2004 | Schuler et al. | |
| 2004/0243182 A1 | 12/2004 | Cohen et al. | |
| 2004/0249416 A1 | 12/2004 | Yun et al. | |
| 2005/0021092 A1 | 1/2005 | Yun et al. | |
| 2005/0021102 A1 | 1/2005 | Ignagni et al. | |
| 2005/0096702 A1 | 5/2005 | Denker et al. | |
| 2005/0137645 A1 | 6/2005 | Voipio et al. | |
| 2005/0288728 A1 | 12/2005 | Libbus et al. | |
| 2006/0009798 A1 | 1/2006 | Callister et al. | |
| 2006/0058852 A1 | 3/2006 | Koh et al. | |
| 2006/0155344 A1 | 7/2006 | Rezai et al. | |
| 2006/0224211 A1 | 10/2006 | Durand et al. | |
| 2006/0229677 A1 | 10/2006 | Moffitt et al. | |
| 2006/0247729 A1 | 11/2006 | Tehrani et al. | |
| 2006/0282127 A1 | 12/2006 | Zealear | |
| 2006/0282131 A1 | 12/2006 | Caparso et al. | |
| 2006/0282145 A1 | 12/2006 | Caparso et al. | |
| 2006/0293720 A1 | 12/2006 | DiLorenzo | |
| 2007/0021795 A1 | 1/2007 | Tehrani | |
| 2007/0027496 A1* | 2/2007 | Parnis et al. | 607/42 |
| 2007/0060954 A1* | 3/2007 | Cameron et al. | 607/2 |
| 2007/0100333 A1 | 5/2007 | Jackson et al. | |
| 2007/0106339 A1 | 5/2007 | Errico et al. | |
| 2007/0118183 A1 | 5/2007 | Gelfand et al. | |
| 2007/0156198 A1 | 7/2007 | Rossing et al. | |
| 2007/0156199 A1 | 7/2007 | Koh et al. | |
| 2007/0173893 A1 | 7/2007 | Pitts | |
| 2007/0203527 A1* | 8/2007 | Ben-David et al. | 607/14 |
| 2007/0213782 A1 | 9/2007 | Shaw | |
| 2007/0255379 A1 | 11/2007 | Williams et al. | |
| 2008/0039904 A1 | 2/2008 | Bulkes et al. | |

OTHER PUBLICATIONS

Karashurov et l., "Radio Frequency Electrostimulation of the Gangliated Cord of the Sympathetic Nerve in Patients with Bronchial Asthma", *Surgery (Khigurgiia)*, 2000, 1:44-46.

Gudovsky et al., "Surgical Treatment of Bronchial Asthma", *Surgery (Khigurgiia)*, 2002, 7:14-18.

Karashurov et al., "Evolution of Surgical Treatment of Bronchial Asthma", *Surgery (Khigurgiia)*, 1999, 11:57-60.

* cited by examiner

APPARATUS AND METHOD FOR TREATING PULMONARY CONDITIONS

RELATED APPLICATIONS

This application is a divisional of U.S. patent application Ser. No. 12/129,734, filed May 30, 2008, which is a continuation-in-part of U.S. patent application Ser. No. 12/016,115, filed Jan. 17, 2008. This application also claims priority from U.S. Provisional Patent Application Ser. No. 60/932,248, filed May 30, 2007, and U.S. patent application Ser. No. 11/121,006, filed May 4, 2005. The subject matter of the aforementioned applications is incorporated herein by reference in their entireties.

TECHNICAL FIELD

The present invention relates to an apparatus and method for treating pulmonary conditions, and more particularly to an implantable medical device for delivering electric current to a target site and effecting a change in the autonomic nervous system of a subject.

BACKGROUND OF THE INVENTION

Diseases and disorders of the pulmonary system are among the leading causes of acute and chronic illness in the world. Pulmonary diseases or disorders may be organized into various categories, including, for example, breathing rhythm disorders, obstructive diseases, restrictive diseases, infectious diseases, pulmonary vasculature disorders, pleural cavity disorders, and others. Pulmonary dysfunction may involve symptoms such as apnea, dyspnea, changes in blood or respiratory gases, symptomatic respiratory sounds, e.g., coughing, wheezing, respiratory insufficiency, and/or general degradation of pulmonary function, among other symptoms.

A variety of methods are currently used to treat pulmonary diseases and disorders including, for example, the use of pharmacological compositions, such as albuterol, and surgical methods, such as lung volume reduction surgery. Another method used to treat pulmonary diseases and disorders involves electrostimulation of various nerves, such as the vagus and phrenic nerves to modulate pulmonary function. Such electrostimulation methods, however, are often highly invasive and offer only short-term symptomatic relief.

SUMMARY OF THE INVENTION in one aspect of the present invention, an apparatus for positioning at a target site and for treating a pulmonary condition in a subject includes a fluid exchange catheter for insertion into a tracheo-bronchial tree and an inflatable balloon coupled to the fluid exchange catheter. At least a portion of the inflatable balloon is for engaging a luminal wall of the tracheo-bronchial tree at the target site. The apparatus further includes an energy delivery mechanism operably coupled to the inflatable balloon. The energy delivery mechanism includes at least one energy delivery member for delivering electrical energy to the target site.

In another aspect of the present invention, a method is provided for treating a pulmonary condition in a subject. One step of the method includes providing an apparatus for positioning at a target site innervated by at least one nerve of the autonomic nervous system (ANS). The apparatus includes a fluid exchange catheter, an inflatable balloon coupled to the fluid exchange catheter, and an energy delivery mechanism including at least one energy delivery member for delivering electrical energy to the target site. An expansion medium is delivered to the apparatus so that the inflatable balloon is sufficiently inflated to sandwich at least a portion of the at least one energy delivery member between the inflatable balloon and a luminal wall of the tracheo-bronchial tree at the target site. Electrical energy is then delivered to the at least one energy delivery member to effect a change in the ANS of the subject.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1A:
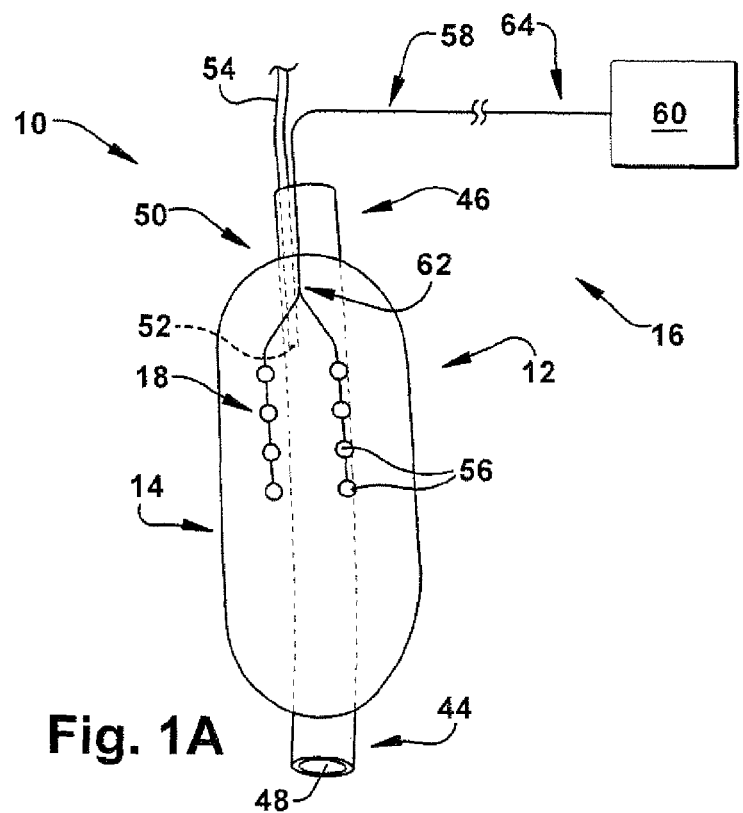
FIG. 1A is a perspective view of an apparatus in a collapsed configuration for treating a pulmonary condition constructed in accordance with the present invention.
Figure 1B:
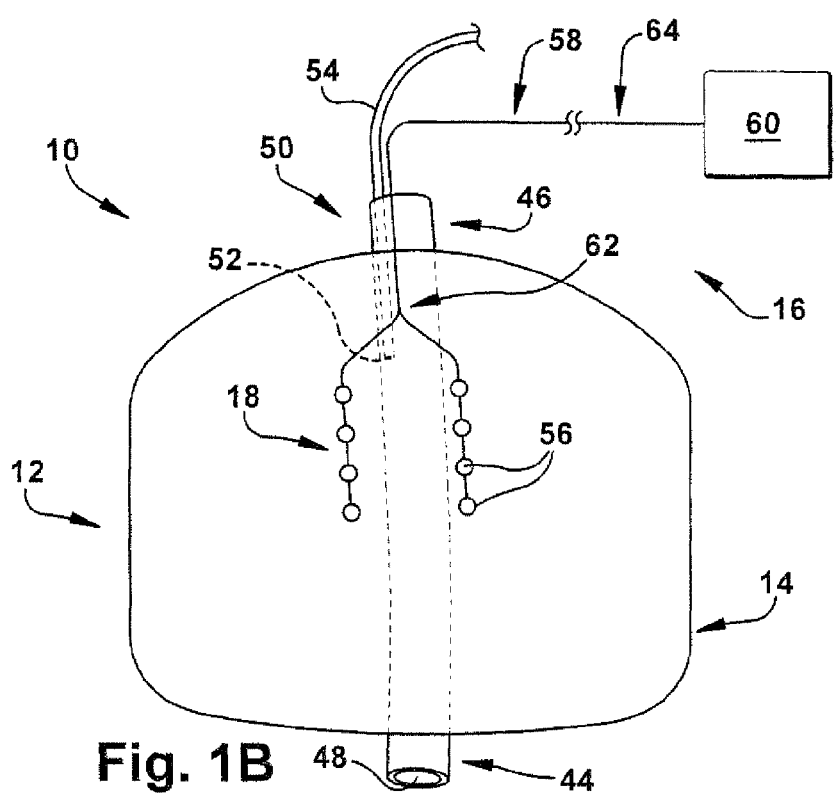
FIG. 1B is a perspective view of the apparatus in FIG. 1A in an expanded configuration.

The present invention relates to an apparatus and method for treating pulmonary conditions, and more particularly to an implantable medical device for delivering electric current to a target site and effecting a change in the autonomic nervous system of a subject. As representative of the present invention, FIGS. 1A-B illustrate an apparatus 10 for treating pulmonary conditions. The apparatus 10 comprises a fluid exchange catheter 12, an inflatable balloon 14 coupled to the catheter, and an energy delivery mechanism 16 including at least one energy delivery member 18 for delivering electrical energy to a target site.

Unless otherwise defined, all technical terms used herein have the same meaning as commonly understood by one of ordinary skill in the art to which the present invention pertains.

In the context of the present invention, the term "pulmonary condition" refers to both infection- and non-infection-induced disease and dysfunction of the respiratory system. Non-limiting examples of pulmonary conditions include genetic conditions, acquired conditions, primary conditions, secondary conditions, asthma, chronic obstructive pulmonary disease, cystic fibrosis, bronchiolitis, pneumonia, bronchitis, emphysema, adult respiratory distress syndrome, allergies, lung cancer, small cell lung cancer, primary lung cancer, metastatic lung cancer, brochiectasis, bronchopulmonary dysplasia, chronic bronchitis, chronic lower respiratory diseases, croup, high altitude pulmonary edema, pulmonary fibrosis, interstitial lung disease, reactive airway disease, lymphangioleiomyomatosis, neonatal respiratory distress syndrome, parainfluenza, pleural effusion, pleurisy, pneumothorax, primary pulmonary hypertension, psittacosis, pulmonary edema secondary to various causes, pulmonary embolism, pulmonary hypertension secondary to various causes, respiratory failure secondary to various causes, sleep apnea, sarcoidosis, smoking, stridor, acute respiratory distress syndrome, infectious diseases, SARS, tuberculosis, psittacosis infection, Q fever, parainfluenza, respiratory syncytial virus, combinations thereof, and conditions caused by any one or combination of the above.

As used herein, the term "target site" refers to a desired anatomical location at which the apparatus 10 may be positioned. The target site can comprise a variety of anatomical locations, including intraluminal locations innervated by at least one nerve. Target sites contemplated by the present invention are illustrated in FIGS. 2A-7 and are described in further detail below.

As used herein, the term "tracheo-bronchial tree" refers to the upside-down, tree-like bodily structure comprised of the trachea and the bronchi.

As used herein, the term "autonomic nervous system" or "ANS" refers to the part of the peripheral nervous system that controls homeostasis and adjusts or modifies some physiological functions in response to stress. The ANS helps to regulate blood pressure and vessel size, the heart's electrical activity and ability to contract, and the bronchium's diameter in the lungs. Additionally, the ANS regulates the movement and work of the stomach, intestine and salivary glands, the secretion of insulin, and urinary and sexual functions. The ANS acts through a balance of its two components, the sympathetic nervous system (SNS) and the parasympathetic nervous system (PNS).

As used herein, the term "parasympathetic nervous system" or "PNS" refers to the part of the ANS originating in the brain stem and the lower part of the spinal cord that, in general, inhibits or opposes the physiological effects of the SNS (e.g., stimulating digestive secretions, slowing the heart, constricting the pupils, and dilating blood vessels).

As used herein, the term "sympathetic nervous system" or "SNS" refers to the part of the ANS originating in the thoracic and lumbar regions of the spinal cord that generally inhibits or opposes the physiological effects of the PNS.

A brief discussion of the relevant neurophysiology is provided to assist the reader with understanding the present invention. The ANS regulates "involuntary" organs. The ANS includes the SNS and the PNS. The SNS is affiliated with stress and the "fight-or-flight response" to emergencies. The PNS is affiliated with relaxation and the "rest-and-digest response." The ANS maintains normal internal function and works with the somatic nervous system. Autonomic balance reflects the relationship between parasympathetic and sympathetic activity. A change in autonomic balance is reflected in changes in heart rate, heart rhythm, contractility, remodeling, inflammation and blood pressure. Changes in autonomic balance can also be seen in other physiological changes, such as changes in abdominal pain, appetite, stamina, emotions, personality, muscle tone, sleep, and allergies.

A more particular description of the neuroanatomy and neurophysiology of which the present invention pertains is presented below.

Anatomy of Tracheo-Bronchial Tree

The trachea 20 (FIG. 3) is a cartilaginous and membranous tube that is part of the respiratory passage. It descends from the larynx (not shown), beginning at the level of C6 (not shown), and then descends along the midline through the neck (not shown) and thorax (not shown) until it reaches its point of bifurcation at the level of T4 (not shown). The trachea 20 is about 10 cm long and 2 cm in diameter. It is covered by the pretracheal fascia. The walls of the trachea 20 are formed from fibrous tissue, and this tissue is reinforced by the presence of 15-20 cartilaginous C-shaped rings. It is flattened posteriorly and supported along its 10- to 15-cm length by 16 to 20 horseshoe-shaped cartilaginous rings until bifurcating into right and left main bronchi 22 and 24 at the level of the fifth thoracic vertebra (not shown). The cross-sectional area of the trachea 20 is considerably larger than that of the glottis (not shown), and may be more than 150 mm$^2$ and as large as 300 mm$^2$. This incompletion allows for the trachea 20 to lie on the esophagus 26 (FIG. 4) through its course.

In the neck, the trachea 20 lies anterior to the esophagus 26 with the recurrent laryngeal nerves (not shown) situated laterally in the groove between the two. The trachea 20 lies posterior to the cervical fascia and the infrahyoid muscles (not shown), and anteriorly it is crossed by the isthmus (not shown) of the thyroid gland (not shown) and the jugular venous arch (not shown). Lateral to the trachea 20 are the lateral lobes (not shown) of the thyroid gland, the inferior thyroid artery (not shown), and the carotid sheath (not shown). The trachea 20 receives its blood supply from the inferior thyroid arteries (not shown). Its lymph drains into the pretracheal and paratracheal lymph nodes (not shown). Nerve supply to the trachea 20 comes via the vagi (not shown), the recurrent laryngeal nerves (not shown), and the sympathetic trunks 28.

Nerve Supply of the Tracheo-Bronchial Tree and Respiratory System

Figure 2A:
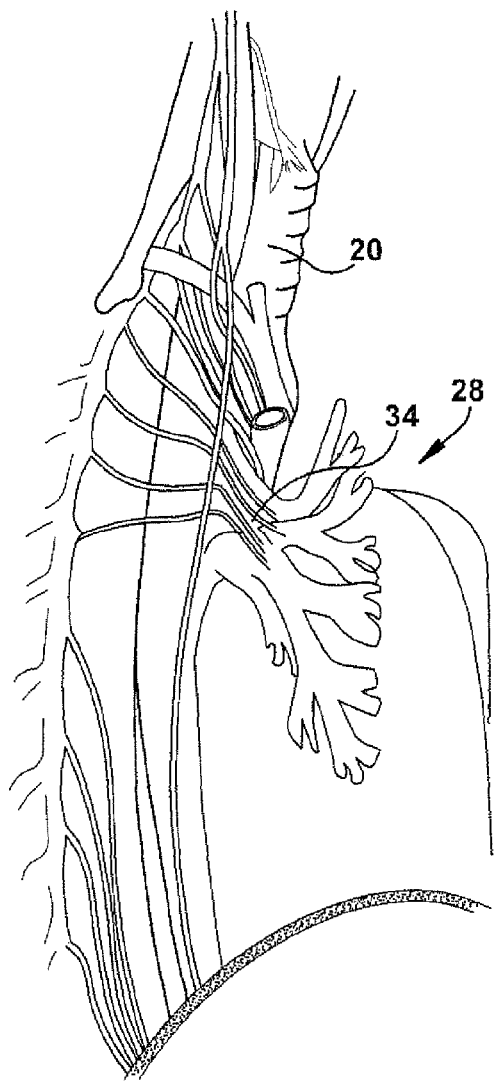
FIG. 2A is a schematic illustration showing the major nerves contributing to the pulmonary plexus.
Figure 2B:
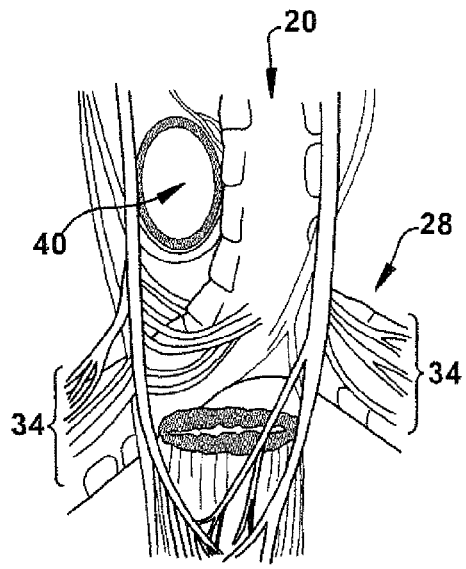
FIG. 2B is a magnified schematic illustration showing a posterior view of the pulmonary plexus.

The pulmonary plexus 30 has two structural divisions: the anterior and posterior plexuses 32 and 34, which are functional divisions of the SNS and the PNS, respectively. The tracheo-bronchial tree 36 and the lungs (not shown) are supplied from the anterior pulmonary plexus 32 (FIG. 2C) and the posterior pulmonary plexus 34 (FIG. 2B). The filaments from the anterior and posterior pulmonary plexuses 32 and 34 accompany the bronchial tubes, supplying efferent fibers to the bronchial muscle and afferent fibers to the bronchial mucous membrane and probably to the alveoli of the lung. Small gangha are found upon these nerves. The pulmonary plexus 30 thus has three major inputs coming from sympathetic ganglia, and parasympathetic or vagal coming directly from the cardiac plexus (not shown).

Sympathetic Component of the Pulmonary Plexus

The thoracic portion 38 (FIG. 3) of the sympathetic trunk 28 consists of a series of ganglia, which usually correspond in number to that of the vertebrae; but, on account of the occasional coalescence of two ganglia, their number is uncertain. The thoracic ganglia rest against the heads of the ribs (not shown), and are covered by the costal pleura; the last two, however, are more anterior than the rest and are placed on the sides of the bodies of the eleventh and twelfth thoracic vertebrae. The ganglia are small in size and of a grayish color. The first, larger than the others, is of an elongated form and frequently blended with the inferior cervical ganglion. They are connected together by the intervening portions of the sympathetic trunk 28. Two rami communicantes, a white and a gray, connect each ganglion with its corresponding spinal nerve. The branches from the upper five thoracic ganglia are very small; they supply filaments to the thoracic aorta and its branches. Twigs from the second, third, fourth and fifth (occasionally sixth and seventh) ganglia enter the posterior pulmonary plexus. The branches from the lower seven thoracic ganglia are large and white in color; they distribute filaments to the aorta and unite to form the greater, the lesser, and the lowest splanchnic nerves (not shown).

Parasympathetic Components of the Pulmonary Plexus

Parasympathetic innervations come through the vagal branches that contribute to the pulmonary plexus 30, and include the anterior bronchial branches (not shown) and the posterior bronchial branches (not shown). The anterior bronchial branches (rami bronchiales anteriores, anterior or ventral pulmonary branches) are two or three in number, of small size, and are distributed on the anterior surface of the root of the lung. They join with filaments from the sympathetic trunk 28 and form the anterior pulmonary plexus 32.

The posterior bronchial branches (rami bronchiales posteriors, posterior or dorsal pulmonary branches) are more numerous and larger than the anterior bronchial branches, and are distributed on the posterior surface of the root of the lung. They are joined by filaments from the third and fourth (sometimes also from the first and second) thoracic ganglia of the sympathetic trunk 28, and form the posterior pulmonary plexus 34. Branches from this plexus 34 accompany the ramifications of the bronchi through the substance of the lung.

Inputs from the Cardiac Plexus

The cardiac plexus is situated at the base of the heart (not shown) and is divided into a superficial part, which lies in the concavity of the aortic arch 40, and a deep part between the aortic arch and the trachea 20. The two parts are closely connected, however. The superficial part of the cardiac plexus lies beneath the aortic arch 40, in front of the right pulmonary artery (not shown). It is formed by the superior cardiac branch (not shown) of the left sympathetic and the lower superior cervical cardiac branch (not shown) of the left vagus. A small ganglion, the cardiac ganglion of Wrisberg (not shown), is occasionally found connected with these nerves at their point of junction. The superficial part of the cardiac plexus gives branches: (a) to the deep part of the plexus; (b) to the anterior coronary plexus; and (c) to the left anterior pulmonary plexus 32.

The deep part of the cardiac plexus is situated in front of the bifurcation of the trachea 20, above the point of division of the pulmonary artery, and behind the aortic arch 40. It is formed by the cardiac nerves derived from the cervical ganglia of the sympathetic and the cardiac branches of the vagus and recurrent nerves. The only cardiac nerves which do not enter into the formation of the deep part of the cardiac plexus are the superior cardiac nerve of the left sympathetic and the lower of the two superior cervical cardiac branches from the left vagus, which pass to the superficial part of the plexus.

The branches from the right half of the deep part of the cardiac plexus pass, some in front of, and others behind the right pulmonary artery. The former, the more numerous, transmit a few filaments to the anterior pulmonary plexus 32 and are then continued onward to form part of the anterior coronary plexus. Those behind the pulmonary artery distribute a few filaments to the right atrium, and are then continued onward to form part of the posterior coronary plexus (not shown). The left half of the deep part of the plexus is connected with the superficial part of the cardiac plexus, gives filaments to the left atrium and to the anterior pulmonary plexus 32, and continues to form the greater part of the posterior coronary plexus.

Structural and Functional Divisions of the Pulmonary Plexus

Figure 2C:
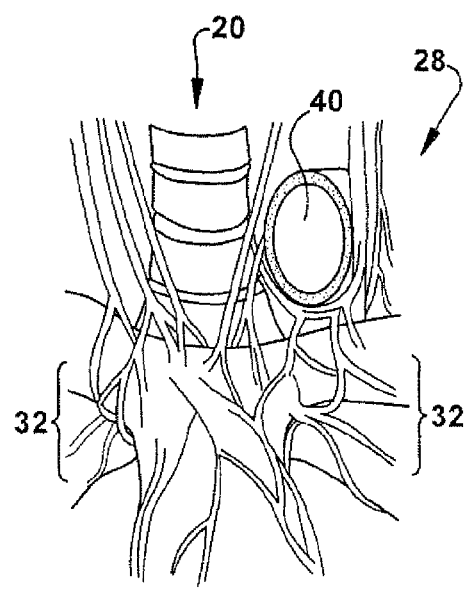
FIG. 2C is a magnified schematic illustration showing an anterior view of the pulmonary plexus.
Figure 3:
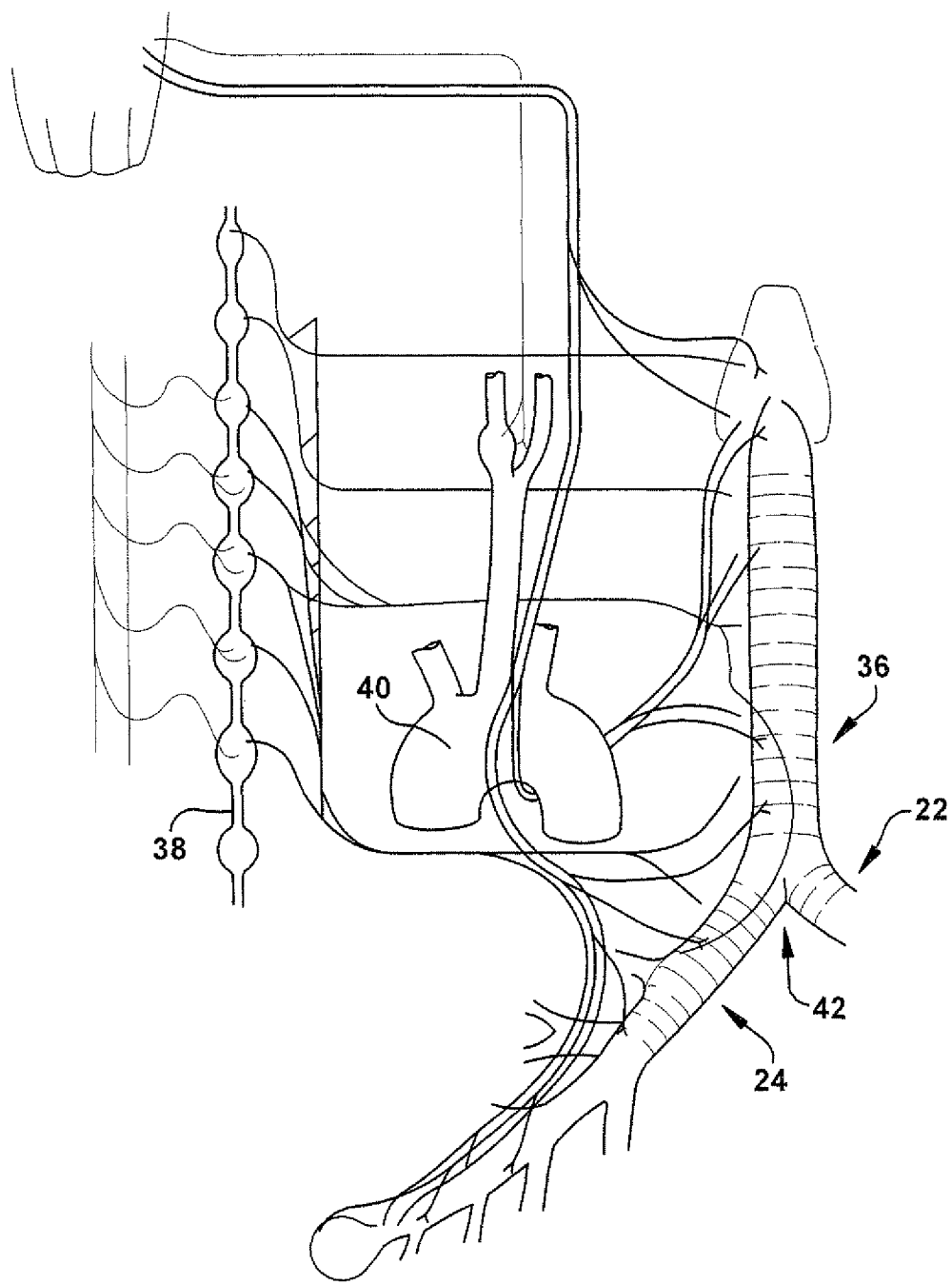
FIG. 3 is a schematic representation of the tracheo-bronchial tree showing the inputs from the thoracic sympathetic trunk.
Figure 4:
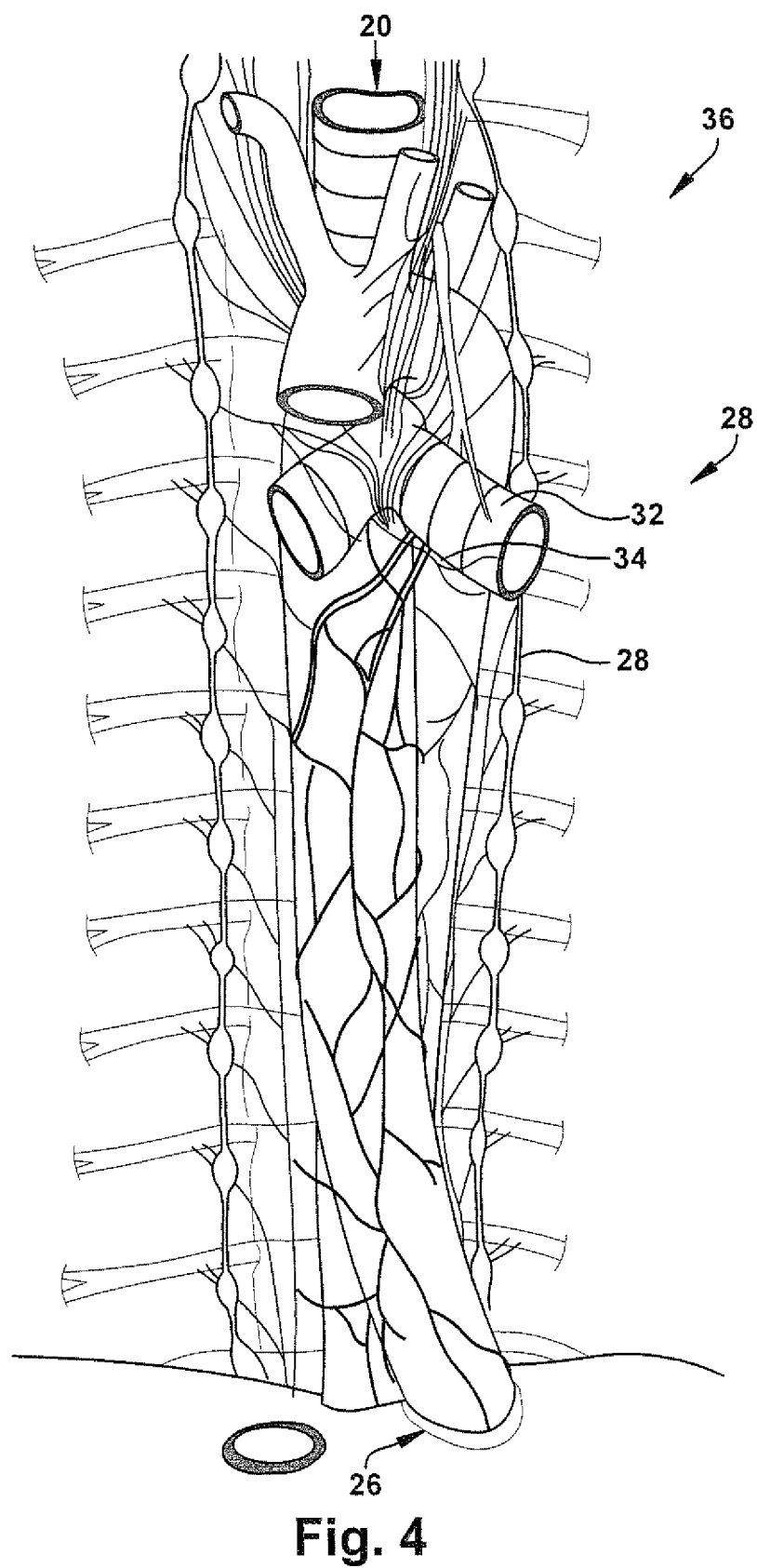
FIG. 4 is a schematic view showing the arrangement of the trachea, esophagus, and aortic arch.

The pulmonary plexus 30 is divided into the anterior and posterior 32 and 34 divisions. The anterior part 32 lies over the tracheal bifurcation 42 (or carina) near the superior aspect of the pulmonary trunk behind the arch of aorta 40 (FIG. 2C). The posterior part 34 lies on the posterior wall of trachea 20 between the trachea and esophagus 26 (FIG. 2B). The anterior part 32 is primarily sympathetic while the posterior part 34 is primarily parasympathetic in function.

Once the plexus 30 enters the tracheo-bronchial tree 36, it further divides into peribronchial and perivascular parts (not shown in detail). The peribronchial plexus is mainly formed by the branches from the recurrent laryngeal and vagus nerves passing to the trachea 20, which then divides and rejoins to form a wide-meshed plexus on the outer sides of the cartilages. This network, containing a few small ganglia, is inconspicuous anteriorly but is well marked posteriorly where it lies on the external elastic lamina.

Filaments from the posterior parts of this plexus pass into the external elastic lamina of the trachea 20 and form, just behind the trachealis muscle, a well-defined longitudinal chain of nerves with scattered ganglia. A wider-meshed plexus, with small ganglia at some of its nodes, is formed in the substance of the trachealis muscle. This could be termed a "primary plexus", for within its meshes is found a finer "secondary plexus" which, in turn, contributes to the still finer fibers of a "tertiary plexus" running parallel to the muscle fibers.

The primary plexus extends in depth through the substance of the trachealis muscle and eventually appears in the tissues of the submucosa. Besides sinking through the muscle, this plexus provides further lateral branches which merge imperceptibly with the fibers that run between and internal to the cartilage plates. Thus, there is a plexus in the muscle continuous with a plexus inside and between the cartilage plates, and this in turn is continuous with the nerves of the submucosa anterior to the trachealis muscle.

Function of the Sympathetic and Parasympathetic Divisions

Sympathetic, parasympathetic, non-adrenergic, and non-cholinergic pathways innervate airway smooth muscle and can produce either bronchoconstriction or bronchodilation when they are activated or inhibited. Therefore, the ANS plays a primary role in regulating airway caliber, and its dysfunction is likely to contribute to the pathogenesis of airways diseases. Indeed, parasympathetic activity is known to promote bronchoconstriction of the airways, and an alteration of muscarinic receptors could lead to an increase of airway hyperresponsiveness (AHR) and then to bronchoconstriction. Moreover, airway inflammation, which is a characteristic feature of bronchial asthma, might alter both the contractile properties and the autonomic regulation of airway smooth muscle. These findings support the hypothesis that autonomic dysfunction and/or dysregulation contributes to the pathogenesis of AHR.

Airway tone is influenced by cholinergic neural mechanisms, adrenergic mechanisms, and by more recently described neural mechanisms which are non-adrenergic and non-cholinergic. Sympathetic innervation to human airways is to the smooth muscle and through ganglia to submucosal glands and bronchial vessels. Airway tone may also be influenced by circulating adrenaline, and there is some evidence that adrenaline secretion may be impaired in asthma. Beta-adrenoceptors (which are almost entirely of the beta 2-subtype) are localized to many cell types in airways. Beta-agonist may be beneficial in airway obstruction, not only by directly relaxing airway smooth muscle (from trachea to terminal bronchioles), but also by inhibiting mast cell mediator release, modulating cholinergic nerves, reducing bronchial edema, and reversing defects in mucociliary clearance.

Alpha-adrenoceptors, which are bronchoconstricting, may be activated by inflammatory mediators and disease. Alpha-agonists can cause bronchoconstriction in asthmatic subjects; however, alpha-antagonists have little effect, which questions the role of alpha-receptors in asthma. Non-cholinergic nerves, which relax human airways, have been demonstrated in vitro. Although the neurotransmitter is not certain, there is now convincing evidence that it may be vasoactive intestinal peptide (VIP) and a related peptide histidine methionine (PHM). VIP and PHM immuno-active nerves are found in human airways, and both peptides potently relay human airways in vitro.

Referring again to FIGS. 1A and 1B, the apparatus 10 for treating pulmonary conditions includes a fluid exchange catheter 12, an inflatable balloon 14 coupled to the catheter, and an energy delivery mechanism 16 including at least one energy delivery member 18 for delivering electrical energy to a target site. The fluid exchange catheter 12 includes an elongated, tube-like structure with a distal end portion 44, a proximal end portion 46, and a lumen 48 extending between the end portions. The fluid exchange catheter 12 can have a rigid, semi-rigid, or flexible configuration to facilitate positioning of the apparatus 10 in the tracheo-bronchial tree 36 of the subject. The fluid exchange catheter 12 can be made of any one or combination of known medical grade materials including, for example, plastic polymers, hardened plastic, carbon fiber, silicon, polyurethane, and the like.

The fluid exchange catheter 12 includes a fluid delivery mechanism 50 for selectively inflating the balloon 14. As shown in FIGS. 1A-B, the fluid delivery mechanism 50 comprises at least one opening 52 disposed on the fluid exchange catheter 12. The opening 52 extends through the wall of the fluid exchange catheter 12 so that the lumen 48 of the fluid exchange catheter and an interior volume of the balloon 14 are in fluid communication with one another. A fluid delivery line 54 is operably coupled to the opening 52 and extends outwardly from the proximal end portion 46 of the fluid exchange catheter 12. The fluid delivery line 54 may be coupled with a fluid delivery source (not shown) for delivering an expansion medium to the balloon 14. As described in more detail below, the fluid delivery line 54 is used to facilitate movement of an expansion medium to selectively inflate and deflate the balloon 14.

The fluid exchange catheter 12 is adapted to facilitate fluid exchange between the lungs of a subject and the ambient environment when the apparatus 10 is implanted in the tracheo-bronchial tree 36 of the subject. When the apparatus 10 is implanted in the tracheo-bronchial tree 36, for example, the fluid exchange catheter 12 exchanges ambient air with expired air from the lungs of the subject. It will be appreciated that the fluid exchange catheter 12 may also function to deliver a select fluid to the lungs of the subject. For example, a fluid delivery source, such as an oxygen tank may be operably connected to the proximal end portion 46 of the fluid exchange catheter 12 to deliver oxygen to the subject. It will also be appreciated that other fluids, such as an anesthetic may additionally or optionally be delivered to the subject via the fluid exchange catheter 12.

As shown in FIGS. 1A-B, the apparatus 10 further includes an inflatable balloon 14 coupled to the fluid exchange catheter 12. The balloon 14 is operably coupled to the fluid exchange catheter 12 so that the balloon may be selectively collapsed (FIG. 1A) and expanded (FIG. 1B). The collapsed configuration of the balloon 14 facilitates placement of the apparatus 10 in the tracheo-bronchial tree 36, while the expanded configuration allows at least a portion of the balloon to engage a luminal wall of the tracheo-bronchial tree at a target site. The balloon 14 is comprised of a thin bladder made of a flexible polymer material such polyimide, polyurethane, PET, PTFE, ePTFE, or the like.

As discussed above, the interior volume of the balloon 14 is in fluid communication with the fluid delivery line 54. An expansion medium can be selectively delivered to the interior volume of the balloon 14 to inflate and deflate the balloon. The expansion medium can comprise a compressible fluid, such as air. The expansion medium may alternatively comprise an incompressible fluid, such as water, saline solution, or the like. Infusion of the expansion medium into the balloon 14 may be accomplished by the fluid delivery source. Examples of fluid delivery sources can include fluid-infusion pumps or calibrated syringes driven by stepper motor or by hand. Alternatively, for a compressible expansion medium, pressurized air or gas may also be used. It will be appreciated that a means (not shown) for determining the amount of expansion medium transferred to the balloon 14, such as a calibrated syringe, may also be included as part of the present invention. For example, a mass or volume flow meter may be coupled to the fluid delivery source for simultaneously measuring the amount of expansion medium in the balloon 14 as it is inflated.

The apparatus 10 also includes an energy delivery mechanism 16 operably coupled to the balloon 14. The energy delivery mechanism 16 includes at least one energy delivery member 18 for delivering electrical energy to a target site. Energy delivery members 18 are operably secured to the balloon 14 so that a portion of each of the energy delivery members is in contact with the target site when the apparatus 10 is implanted in the trachea-bronchial tree 36.

The energy delivery members 18 can be operably secured to the balloon 14 using a suitable adhesive, stitching, or tape, for example. The energy delivery members 18 are made of an electrically conductive material, such as platinum or platinum-iridium. It will be appreciated that any number of energy delivery members 18 may be operably secured to the balloon 14 and, further, that the energy delivery members can have any suitable shape, such as a rectangular or ovoid shape. It will be further appreciated that the energy delivery members 18 may also be disposed about the inflatable balloon 14 in any desired configuration. For example, the energy delivery members 18 may be arranged such that one energy delivery member is disposed about the inflatable balloon 14 approximately 180° from another energy delivery member.

As shown in FIGS. 1A-B, the energy delivery members 18 of the energy delivery mechanism 16 comprise a plurality of electrodes 56 operably secured to the inflatable balloon 14. The electrodes 56 have a flat, disc-like shape and are centrally disposed about the balloon 14. It will be appreciated, however, that the electrodes 56 may have any shape and size, including, for example, a triangular shape, a rectangular shape, an ovoid shape, and/or a band-like shape (e.g., a split band configuration), and are not limited to the shapes and sizes, illustrated in FIGS. 1A-B. The electrodes 56 may be made of any material capable of conducting an electrical current, such as platinum, platinum-iridium, or the like.

As shown in FIGS. 1A-B, the electrodes 56 can extend around only a portion of the balloon 14 in a parallel fashion. It will be appreciated, however, that the electrodes 56 may extend around only a portion or the entire circumference of the balloon 14 in a sinusoidal, radial, or helical fashion (not shown). Alternatively, the entire surface of the balloon 14 may be covered with the electrodes 56.

To facilitate focal delivery of electrical energy to a target site, the electrodes 56 may wrap around the circumference of the balloon 14 any number of times to establish a desired electrode contact and coverage. Additionally or optionally, the entire surface area of the electrodes 66 may be conductive or, alternatively, only a portion of the surface area of the electrodes may be conductive. By modifying the conductivity of the surface of the electrodes 56, the surface area of the electrodes that contact a target site may be selectively modified to facilitate focal delivery of electrical energy to the target site.

The energy delivery mechanism 16 further includes at least one electrical lead 58 for conveying electrical energy from an energy delivery source 60 to the energy delivery members 18. The electrical lead 58 comprises an electrically conductive wire having distal and proximal end portions 62 and 64. As shown in FIGS. 1A-B, the distal end portion 62 of the electrical lead 58 has a spliced or Y-shaped configuration and is electrically connected to the energy delivery members 18. It will be appreciated, however, that the distal end portion 62 of the electrical lead 58 may have any other configuration suitable to ensure delivery of electrical energy to the energy delivery members 18.

The proximal end portion 64 of the electrical lead 58 is operably connected to the energy delivery source 60. Examples of suitable energy delivery sources 60 include sources capable of delivering RF energy, x-ray energy, microwave energy, ultrasonic energy such as focused ultrasound, high intensity focused ultrasound energy, light energy, electric field energy, magnetic energy, combinations of the same, or the like. The energy delivery source 60 may be directly coupled to the energy delivery members 18 as shown in FIGS. 1A-B or, alternatively, wirelessly coupled (not shown) to the energy delivery members. Alternatively, the energy delivery source 60 can comprise a device capable of harvesting mechanical and/or thermodynamic energy from the body of a subject, such as a piezoelectric device. As described in more detail below, activation of the energy delivery source 60 causes an electrical current to be conducted through the electrical lead 58 and into the energy delivery members 18. This permits delivery of electrical energy to the target site and, depending on the particular target site and the nature of electric current being delivered to the energy delivery members 18, facilitates modulation of the ANS.

Electrical energy can be delivered to the energy delivery members 18 continuously, periodically, episodically, or a combination thereof. For example, electrical energy can be delivered in a unipolar, bipolar, and/or multipolar sequence or, alternatively, via a sequential wave, charge-balanced biphasic square wave, sine wave, or any combination thereof. Electrical energy can be delivered to all the energy delivery members 18 at once or, alternatively, to only a select number of desired energy delivery members. The particular voltage, current, and frequency delivered to the energy delivery members 18 may be varied as needed. For example, electrical energy can be delivered to the energy delivery members 18 at a constant voltage (e.g., at about 0.1 v to about 25 v), at a constant current (e.g., at about 25 microampes to about 50 milliamps), at a constant frequency (e.g., at about 5 Hz to about 10,000 Hz), and at a constant pulse-width (e.g., at about 50 μsec to about 10,000 μsec).

Typically, delivery of electrical energy to the energy delivery members 18 results in activation of at least one nerve at the target site which, in turn, effects a change in the ANS of a subject. Alternatively, deactivation or modulation of electrical energy to the energy delivery members 18 may cause or modify activation of at least one nerve at the target site. For example, electrical energy may be delivered to the energy delivery members 18 and consequently inhibit activation of at least one nerve at or adjacent the target site. Modulating the electrical energy delivered to the energy delivery members 18 may induce a change or changes in the activity, chemistry, and/or metabolism of at least one nerve directly or indirectly associated with the target site.

It should be appreciated, however, that means other than, or in addition to electrical energy, such as chemical or biological means, may also be delivered to the target site and thereby effect a change in the ANS. For example, the apparatus 10 may include at least one therapeutic agent for eluting into the vascular tissue and/or blood stream. The therapeutic agent may be capable of preventing a variety of pathological conditions including, for example, inflammation. Accordingly, the therapeutic agent may include at least one of an antioxidant, a steroid, an anti-apoptotic agent, and/or an anti-inflammatory agent. One example of a therapeutic agent can include Botulinum toxin (e.g., BOTOX).

Optionally or additionally, the therapeutic agent may be capable of treating or preventing other diseases or disease processes, such as microbial infections, for example. In these instances, the therapeutic agent may include an anti-microbial agent and/or a biological agent such as a cell, peptide, or nucleic acid. The therapeutic agent can be simply linked to a surface of the apparatus 10, embedded and released from within polymer materials, such as a polymer matrix, or surrounded by and released through a carrier.

The present invention further provides a method for treating a pulmonary condition in a subject. As used herein, the term "subject" refers to any warm-blooded organism including, but not limited to, human beings, pigs, rats, mice, dogs, goats, sheep, horses, monkeys, apes, rabbits, cattle, etc. The pulmonary condition may be treated by modulating the SNS, the PNS, or both. Suitable target sites for treatment of the pulmonary condition include, without limitation, intraluminal sites proximal to the pulmonary plexus 30, at the pulmonary plexus, and/or distal to the pulmonary plexus.

Target sites at the pulmonary plexus 30 include the anterior pulmonary plexus 32, in which case delivery of electrical energy to the target site will primarily modulate the SNS. As used herein, the term "modulate" or "modulating" refers to causing a change in neuronal activity, chemistry, and/or metabolism. The change can refer to an increase, decrease, or even a change in a pattern of neuronal activity. The term may refer to either excitatory or inhibitory stimulation, or a combination thereof, and may be at least electrical, biological, magnetic, optical or chemical, or a combination of two or more of these. The term "modulate" can also be used to refer to a masking, altering, overriding, or restoring of neuronal activity.

Another target site at the pulmonary plexus 30 includes the posterior pulmonary plexus 34, in which case delivery of electrical energy to the target site will primarily modulate the PNS. To facilitate placement of the apparatus 10 at the target site, at least a portion of the apparatus may be made of a radio-opaque material or include radio-opaque markers (not shown) to facilitate fluoroscopic visualization.

Figure 5:
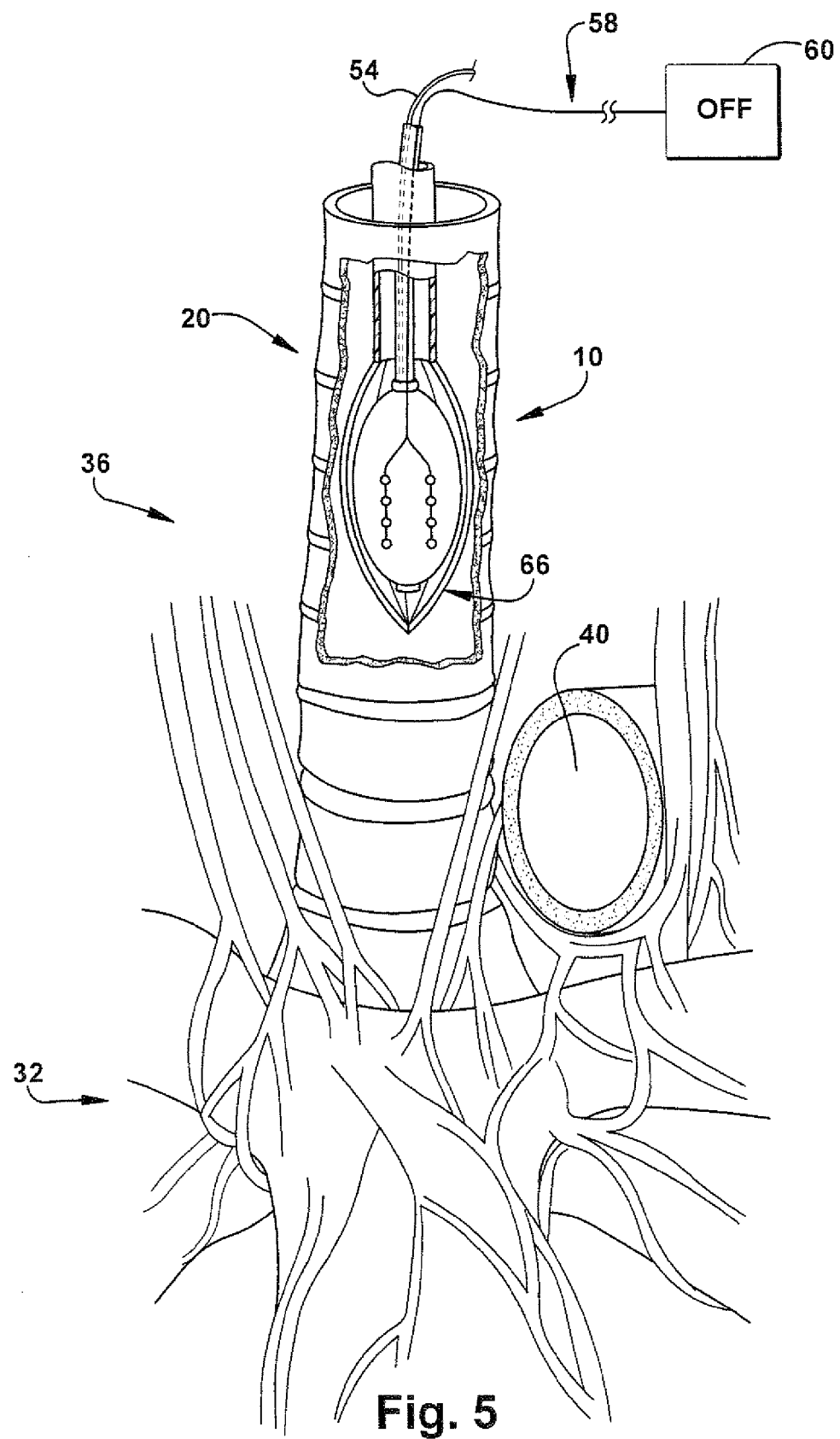
FIG. 5 is a magnified view of FIG. 2C showing the apparatus of FIG. 1A being inserted into the tracheo-bronchial tree.
Figure 6:
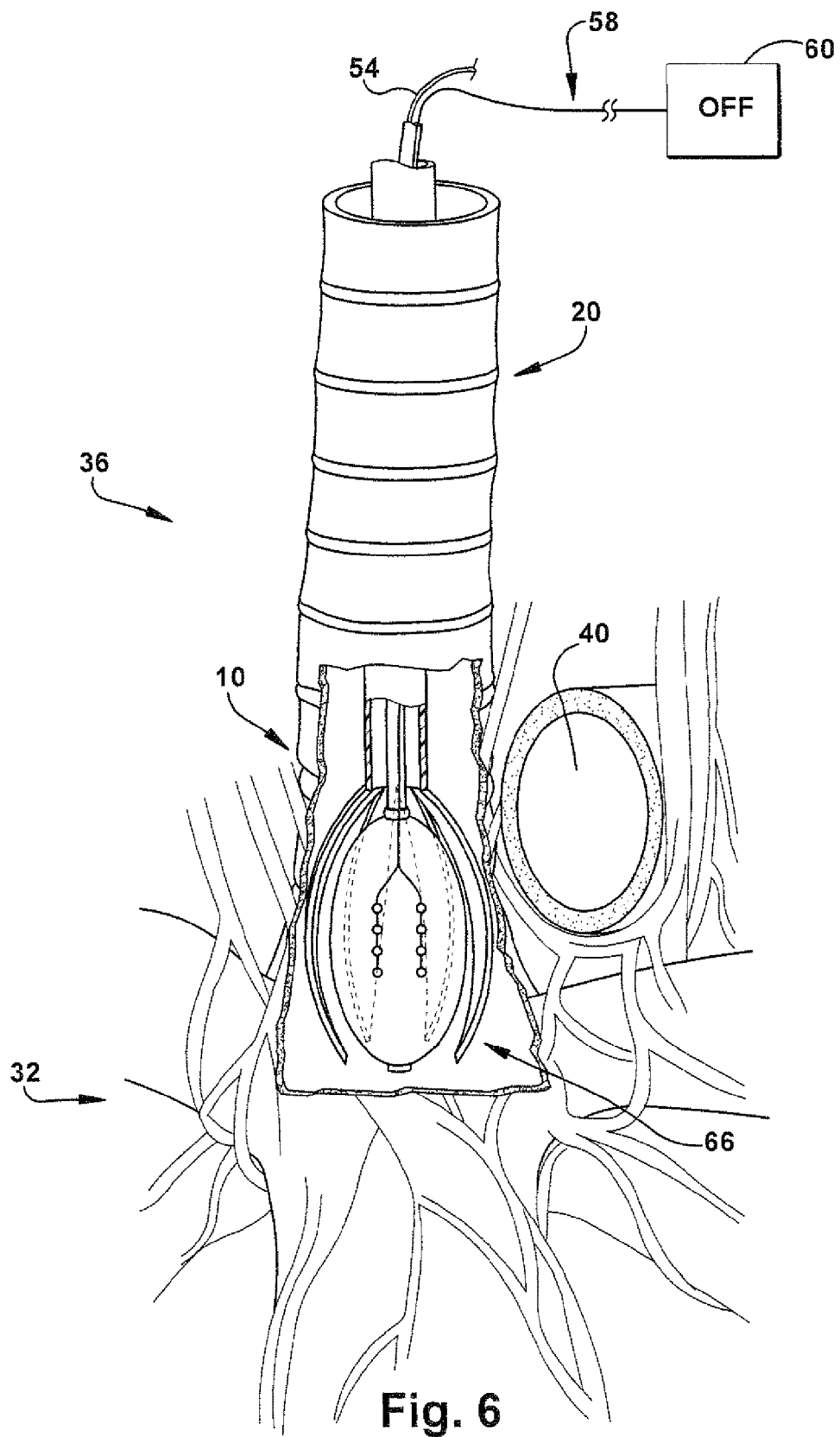
FIG. 6 is a magnified view of FIG. 2C showing the apparatus of FIG. 1A being deployed from a delivery capsule into the trachea-bronchial tree.
Figure 7:
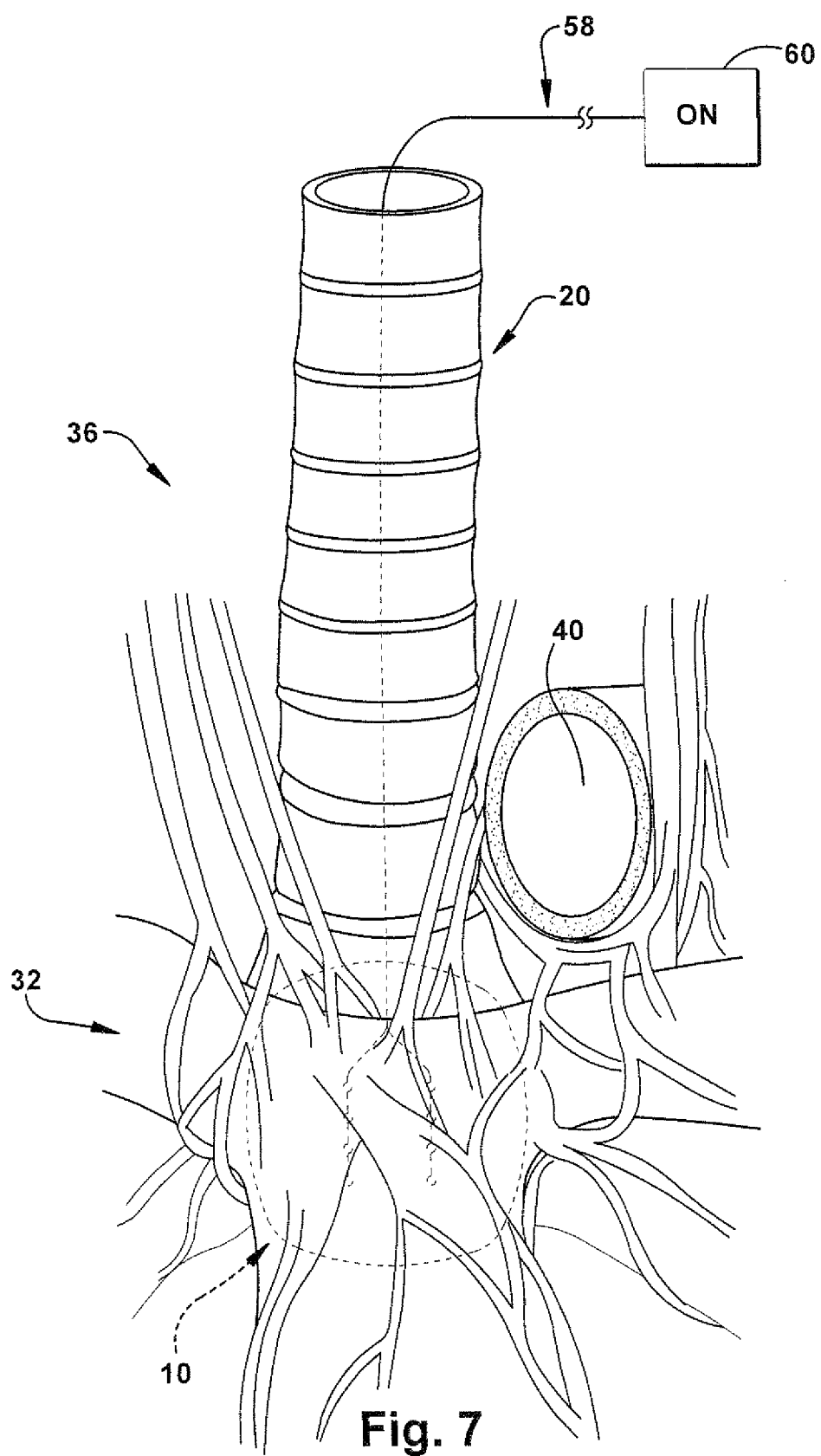
FIG. 7 is a magnified view of FIG. 2C showing the apparatus of FIG. 1B implanted in the tracheo-bronchial tree.

The apparatus 10 may be implanted in a subject suffering from asthma, for example, using a known laryngoscopic approach. Prior to use of the apparatus 10, the dimensions of the target site can be determined. For the purpose of illustration only, the target site can comprise a portion of the intraluminal tracheal wall adjacent the anterior pulmonary plexus 32 (FIGS. 5-7). Various methods and devices for determining the dimensions of the trachea 20, and in particular the intraluminal diameter of the trachea, are known in the art and can include, for example, MRI, CT, X-ray, and fluoroscopy. After determining the dimensions of the trachea 20 at the target site, an appropriately-sized apparatus 10 is chosen. The apparatus 10 is suitably sized, for example, so that the diameter of the balloon 14 in the expanded configuration corresponds to the intraluminal diameter of the trachea 20 at the target site.

As shown in FIG. 5, the apparatus 10 is placed in a delivery capsule 66 and inserted into the trachea 20 of the subject. The delivery capsule 66 is then advanced toward the target site, and the position of the delivery capsule is monitored by fluoroscopy, for example. When the delivery capsule 66 reaches the target site, the delivery capsule releases the apparatus 10 as shown in FIG. 6 and is then withdrawn from the trachea 20.

After withdrawing the delivery capsule 66 from the trachea 20, the position of the apparatus 10 can be adjusted so that the energy delivery members 18 are positioned substantially adjacent the anterior pulmonary plexus 32. As shown in FIG. 7, an energy delivery source 60 is next activated so that electric current is delivered to the energy delivery members 18. It should be appreciated that unwanted collateral stimulation of adjacent tissues may be limited by creating localized cells or electrical fields (i.e., by limiting the electrical field beyond a desired location). Localized cells may be created by, for example, spacing the energy delivery members 18 very close together or biasing the electrical field with conductors (not shown) and/or magnetic fields. For example, electrical fields may be localized or shaped by using energy delivery members 18 with different geometries, by using one or more multiple electrodes 56, and/or by modifying the frequency, pulse-width, voltage, stimulation waveforms, paired pulses, sequential pulses, and/or combinations thereof.

Delivery of electrical energy to the energy delivery members 18 stimulates or activates at least one sympathetic nerve associated with the anterior pulmonary plexus 32. Consequently, the SNS directly relaxes airway smooth muscles of the tracheo-bronchial tree 36. Additionally, stimulation or activation of the SNS inhibits mast cell mediator release by modulating cholinergic nerves, reducing bronchiole edema, and reversing defects in mucociliary clearance. By delivering electrical energy to the energy delivery members 18 and stimulating or activating the SNS, the smooth muscles of tracheo-bronchial tree 36 are relaxed and the asthmatic symptoms of the subject are reduced or eliminated. It will be appreciated that electrical energy may be further delivered to the energy delivery members 18 as needed to eliminate or reduce reoccurring symptoms of asthma in the subject. Once the asthmatic symptoms have been reduced or eliminated, the energy delivery source 60 may be inactivated and the apparatus 10 removed from the tracheo-bronchial tree 36 of the subject.

It will be appreciated that the apparatus 10 described herein can be part of an open- or closed-loop system. In an open-loop system, for example, a physician or subject may, at any time, manually or by the use of pumps, motorized elements, etc. adjust treatment parameters such as pulse amplitude, pulse width, pulse frequency, or duty cycle. Alternatively, in a closed-loop system, electrical parameters may be automatically adjusted in response to a sensed symptom or a related symptom indicative of the extent of the pulmonary condition being treated. In a closed-loop feedback system, a sensor (not shown) that senses a condition (e.g., a metabolic parameter of interest) of the body can be utilized. More detailed descriptions of sensors that may be employed in a closed-loop system, as well as other examples of sensors and feedback control techniques that may be employed are disclosed in U.S. Pat. No. 5,716,377, which is hereby incorporated by reference in its entirety.

It should also be appreciated that incorporating the apparatus 10 as part of a closed-loop system can include placing the apparatus at a target site, detecting a bodily activity associated with a pulmonary condition, and then activating the apparatus to apply electrical energy to the target site in response to the detected bodily activity. Such bodily activity can include any characteristic or function of the body, such as respiratory function (e.g., respiratory rate), body temperature, blood pressure, metabolic activity such as fluid glucose levels, hormone levels, and/or nitrogen, oxygen and/or carbon dioxide levels, cerebral blood flow, pH levels (e.g., in blood, tissue, and other bodily fluids), galvanic skin responses (e.g., perspiration), electrocardiogram, muscle tone in the diaphragm and other muscles, electroencephalogram, nerve action potential, body movement, response to external stimulation, speech, motor activity, ocular activity, cognitive function, and the like.

The analysis of constituents of breath, for example, provides an easily accessible, non-invasive method of monitoring inflammation as a number of by-products of airway inflammation and oxidative stress are found in exhaled air. Accordingly, a closed-loop system can include a sensor for detecting at least one metabolic parameter associated with pulmonary inflammation from the exhaled vapor, of a subject. Examples of the metabolic parameter can include, but are not limited to, eicosanoids (e.g., 8-isoprostanes, leukotriene$_4$ (LTE$_4$), LTC$_4$, LTD$_4$, LTB$_4$, PG, TX), NO-related products (e.g., nitrotyrosine, NO$_2^-$/NO$_3^-$, S-nitrosothiols), hydrogen peroxide, lipid peroxidation products, vasoactive amines, ammonia, cytokines (e.g., IL-1$\beta$, IL-2, IL-6, TNF-$\alpha$, IL-8), and electrolytes (e.g., Na, Cl, Mg, Ca).

From the above description of the invention, those skilled in the art will perceive improvements, changes and modifications. For example, the apparatus 10 may comprise only the inflatable balloon 14 and the energy delivery mechanism 16 so that the fluid exchange catheter 12 and the balloon may be implanted and removed separately from the subject. Such improvements, changes and modifications within the skill of the art are intended to be covered by the appended claims.

Having described the invention, we claim:

1. A method for treating asthma in a subject, said method comprising the steps of:
   providing an apparatus for positioning at a target site innervated by the pulmonary plexus, the apparatus comprising a fluid exchange catheter, an inflatable balloon coupled to the fluid exchange catheter, and an energy delivery mechanism including a plurality of energy delivery members for delivering electrical energy to the target site;
   delivering an expansion medium to the apparatus so that the inflatable balloon is sufficiently inflated to sandwich at least a portion of the plurality of energy delivery members between the inflatable balloon and a luminal wall of the tracheo-bronchial tree at the target site; and
   delivering electrical energy to the plurality of energy delivery members to stimulate the pulmonary plexus and effect a change in the autonomic nervous system (ANS) of the subject and thereby treat the asthma;
   wherein the plurality of energy delivery members is arranged on the inflatable balloon to facilitate focal delivery of the electrical energy to only the pulmonary plexus.

2. The method of claim 1, wherein the target site comprises an inner surface of the trachea adjacent the carina.

3. The method of claim 1, wherein delivery of electrical energy to the at least one energy delivery member effects a change in the parasympathetic nervous system (PNS) of the subject.

4. The method of claim 1, wherein delivery of electrical energy to the at least one energy delivery member effects a change in the sympathetic nervous system (SNS) of the subject.

5. The method of claim 1, wherein delivery of electrical energy to an anterior pulmonary plexus effects a change in the SNS.

6. The method of claim 1, wherein delivery of electrical energy to a posterior pulmonary plexus effects a change in the PNS.

7. The method of claim 1, wherein delivery of electrical energy to an anterior pulmonary plexus effects a change in both the SNS and the PNS.

8. The method of claim 1, wherein delivery of electrical energy to a posterior pulmonary plexus effects a change in both the SNS and the PNS.

9. The method of claim 1, wherein the pulmonary condition is selected from the group consisting of genetic conditions, acquired conditions, primary conditions, secondary conditions, asthma, chronic obstructive pulmonary disease, cystic fibrosis, bronchiolitis, pneumonia, bronchitis, emphysema, adult respiratory distress syndrome, allergies, lung cancer, small cell lung cancer, primary lung cancer, metastatic lung cancer, brochiectasis, bronchopulmonary dysplasia, chronic bronchitis, chronic lower respiratory diseases, croup, high altitude pulmonary edema, pulmonary fibrosis, interstitial lung disease, reactive airway disease, lymphangioleiomyomatosis, neonatal respiratory distress syndrome, parainfluenza, pleural effusion, pleurisy, pneumothorax, primary pulmonary hypertension, psittacosis, pulmonary edema secondary to various causes, pulmonary embolism, pulmonary hypertension secondary to various causes, respiratory failure secondary to various causes, sleep apnea, sarcoidosis, smoking, stridor, acute respiratory distress syndrome, infectious diseases, SARS, tuberculosis, psittacosis infection, Q fever, parainfluenza, and respiratory syncytial virus.

10. The method of claim 1, wherein the entire surface of the inflatable balloon is covered with the multiple energy delivery members.

11. The method of claim 1, wherein the electrical energy delivered to the target site is a charge-balanced bipolar waveform.

12. The method of claim 1, wherein said step of delivering electrical energy to the multiple energy delivery members further includes creating a localized electrical cell to provide focal delivery of the electrical energy to the pulmonary plexus.

13. The method of claim 1, wherein the electrical signal has a frequency of about 5 Hz to about 200 Hz.

14. The method of claim 13, wherein the electrical signal has a frequency of about 5 Hz to about 40 Hz.

15. The method of claim 1, wherein the electrical signal has a current of about 50 µs to about 2000 µs.

16. The method of claim 15, wherein the electrical signal has a current of about 100 µs to about 500 µs.

17. A method for treating chronic obstructive pulmonary disease (COPD) in a subject, said method comprising the steps of:
providing an apparatus for positioning at a target site innervated by the pulmonary plexus, the apparatus comprising a fluid exchange catheter, an inflatable balloon coupled to the fluid exchange catheter, and an energy delivery mechanism including a plurality of energy delivery members for delivering electrical energy to the pulmonary plexus;
delivering an expansion medium to the apparatus so that the inflatable balloon is sufficiently inflated to sandwich at least a portion of the plurality of energy delivery members between the inflatable balloon and a luminal wall of the tracheo-bronchial tree at the target site; and
delivering electrical energy to the plurality of energy delivery members to stimulate the at least one nerve of the ANS and effect a change in the ANS of the subject and thereby treat the COPD;
wherein the plurality of energy delivery members is arranged on the inflatable balloon to facilitate focal delivery of the electrical energy to only the pulmonary plexus.

18. A method for treating adult respiratory distress syndrome (ARDS) in a subject, said method comprising the steps of:
providing an apparatus for positioning at a target site innervated by the pulmonary plexus, the apparatus comprising a fluid exchange catheter, an inflatable balloon coupled to the fluid exchange catheter, and an energy delivery mechanism including a plurality of energy delivery members for delivering electrical energy to the target site;
delivering an expansion medium to the apparatus so that the inflatable balloon is sufficiently inflated to sandwich at least a portion of the plurality of energy delivery members between the inflatable balloon and a luminal wall of the tracheo-bronchial tree at the target site; and
delivering electrical energy to the plurality of energy delivery members to stimulate the pulmonary plexus and effect a change in the ANS of the subject and thereby treat the ARDS;
wherein the plurality of energy delivery members is arranged on the inflatable balloon to facilitate focal delivery of the electrical energy to only the pulmonary plexus.

* * * * *